(12) United States Patent
Zhang (10) Patent No.: US 11,725,483 B2
(45) Date of Patent: Aug. 15, 2023

(54) METHOD AND SYSTEM OF FRACABILITY MEASUREMENT BASED ON CORE FRACTURE DENSITY

(71) Applicant: SAUDI ARABIAN OIL COMPANY, Dhahran (SA)

(72) Inventor: Si-Hai Zhang, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 365 days.

(21) Appl. No.: 16/900,016

(22) Filed: Jun. 12, 2020

(65) Prior Publication Data

US 2021/0389499 A1 Dec. 16, 2021

(51) Int. Cl.
*E21B 41/00* (2006.01)
*G06T 7/00* (2017.01)
(Continued)

(52) U.S. Cl.
CPC .............. *E21B 41/00* (2013.01); *E21B 25/00* (2013.01); *E21B 49/02* (2013.01); *G01N 33/24* (2013.01);
(Continued)

(58) Field of Classification Search
None
See application file for complete search history.

(56) References Cited

U.S. PATENT DOCUMENTS

2008/0130407 A1* 6/2008 Akhtar ............... G01V 1/42
367/9
2013/0236064 A1 9/2013 Li et al.
(Continued)

FOREIGN PATENT DOCUMENTS

CN 104345339 A 2/2015
CN 104677734 A 6/2015
(Continued)

OTHER PUBLICATIONS

International Search Report and Written Opinion issued in Application No. PCT/US2020/047138, dated Mar. 11, 2021 (17 pages).
(Continued)

*Primary Examiner* — Jeffrey J Chow
(74) *Attorney, Agent, or Firm* — Osha Bergman Watanabe & Burton LLP (57) ABSTRACT

A method for generating a fracability model of a subterranean formation. The method includes coring and collecting rock cores from a plurality of geographical locations in the subterranean formation, capturing a plurality of core images of the rock cores, generating, by a computer processor and based on the plurality of core images, a plurality of artificial fracture counts of the rock cores, computing, by the computer processor and based on the plurality of artificial fracture counts, a first fracture density curve corresponding to a first geographical location of the plurality of geographical locations, generating, by the computer processor and based on the first fracture density curve, a first fracability measure curve of the rock cores, and generating, by the computer processor and based at least on the first fracability measure curve, a fracability model of the subterranean formation.

20 Claims, 7 Drawing Sheets

(51) Int. Cl.
    *G06T 7/70* (2017.01)
    *G06F 30/20* (2020.01)
    *E21B 25/00* (2006.01)
    *E21B 49/02* (2006.01)
    *G01N 33/24* (2006.01)
    *G01V 99/00* (2009.01)
    *G06N 7/08* (2006.01)
    *G06T 11/20* (2006.01)
    *G06F 18/214* (2023.01)
    *G06F 18/21* (2023.01)

(52) U.S. Cl.
    CPC .......... *G01V 99/005* (2013.01); *G06F 18/214* (2023.01); *G06F 18/2178* (2023.01); *G06F 30/20* (2020.01); *G06N 7/08* (2013.01); *G06T 7/70* (2017.01); *G06T 7/97* (2017.01); *G06T 11/206* (2013.01); *E21B 2200/20* (2020.05); *G06T 2207/10012* (2013.01); *G06T 2207/30181* (2013.01); *G06T 2207/30242* (2013.01)

(56) References Cited

U.S. PATENT DOCUMENTS

| | | | |
|---|---|---|---|
| 2015/0301223 A1 | 10/2015 | Xu et al. | |
| 2016/0313469 A1 | 10/2016 | Von Gonten et al. | |
| 2017/0023687 A1* | 1/2017 | Sicking | G01V 1/302 |
| 2017/0248719 A1* | 8/2017 | Holman | G01V 11/00 |
| 2018/0094514 A1* | 4/2018 | Leem | E21B 43/26 |
| 2018/0106708 A1* | 4/2018 | Siebrits | G01N 23/046 |
| 2018/0202266 A1* | 7/2018 | Holland | E21B 41/0092 |
| 2018/0259668 A1* | 9/2018 | Gu | G01V 1/50 |
| 2019/0080122 A1 | 3/2019 | Camargo et al. | |
| 2019/0145251 A1* | 5/2019 | Johnson | E21B 43/26 166/250.1 |
| 2019/0234205 A1* | 8/2019 | Arro | G01V 8/02 |
| 2019/0249534 A1* | 8/2019 | Hoeink | G01V 1/50 |
| 2019/0266501 A1* | 8/2019 | Tavares | G06N 5/04 |
| 2020/0309982 A1* | 10/2020 | Jin | G01V 1/50 |
| 2020/0340357 A1* | 10/2020 | Johnson | E21B 43/26 |
| 2020/0386093 A1* | 12/2020 | Klenner | E21B 47/107 |
| 2022/0137247 A1* | 5/2022 | Raterman | G01V 1/288 166/250.1 |

FOREIGN PATENT DOCUMENTS

| | | |
|---|---|---|
| CN | 104865124 A | 8/2015 |
| CN | 105319603 A | 2/2016 |
| CN | 105221141 B | 8/2016 |
| CN | 106769463 A | 5/2017 |
| CN | 107976352 A | 5/2018 |
| CN | 108645596 A | 10/2018 |
| CN | 109164499 A | 1/2019 |
| JP | 2004233304 A | 8/2004 |
| WO | 2016186691 A1 | 11/2016 |

OTHER PUBLICATIONS

Bruland, Amund, "Hard Rock Tunnel Boring", Doctoral Theses at NTNU 1998:81, NTNU Trondheim, vol. 1, 2000 (55 pages).

Dahl, Filip et al., "Classifications of properties influencing the drillability of rocks, based on the NTNU/SINTEF test method", Tunnelling and Underground Space Technology, Elsevier Ltd., vol. 28, Nov. 8, 2011, pp. 150-158 (9 pages).

Jarvie, Daniel M. et al, "Unconventional shale-gas systems: The Mississippian Barnett Shale of north-central Texas as one model for thermogenic shale-gas assessment", AAPG Bulletin, The American Association of Petroleum Geologists, vol. 91, No. 4, Apr. 2007, pp. 475-499 (25 pages).

Mullen, Mike et al., "A Composite Determination of Mechanical Rock Properties for Stimulation Design (What to do When You Don't Have a Sonic Log)", SPE 108139, Society of Petroleum Engineers, Apr. 2007 (13 pages).

Rickman, Rick et al., "A Practical Use of Shale Petrophysics for Stimulation Design Optimization: All Shale Plays are Not Clones of the Barnett Shale", SPE 115258, Society of Petroleum Engineers, Sep. 2008 (11 pages).

Wang, Fred P. and Julia F. W. Gale, "Screening Criteria for Shale-Gas Systems", Gulf Coast Association of Geological Societies Transactions, vol. 59, 2009, pp. 779-793 (15 pages).

* cited by examiner

METHOD AND SYSTEM OF FRACABILITY MEASUREMENT BASED ON CORE FRACTURE DENSITY

BACKGROUND

Hydraulic fracturing is an oil field production technique that involves injecting a pressurized fluid to artificial fracture bedrock formations. For example, the pressurized fluid may be injected into the bedrock formations through an injection well such that hydrocarbons flow through the induced fractures to be collected through a production well. Rock fracability is a measure of easiness to which a formation can be fractured. A core sample is a cylindrical section of a natural substance, such as sediment or rock. Core samples are usually obtained by drilling with a coring bit (e.g., hollow steel tube) into the sediment or rocks.

SUMMARY

In general, in one aspect, the invention relates to a method for generating a fracability model of a subterranean formation. The method includes coring and collecting rock cores from a plurality of geographical locations in the subterranean formation, capturing a plurality of core images of the rock cores, generating, by a computer processor and based on the plurality of core images, a plurality of artificial fracture counts of the rock cores, computing, by the computer processor and based on the plurality of artificial fracture counts, a first fracture density curve corresponding to a first geographical location of the plurality of geographical locations, generating, by the computer processor and based on the first fracture density curve, a first fracability measure curve of the rock cores, and generating, by the computer processor and based at least on the first fracability measure curve, a fracability model of the subterranean formation.

In general, in one aspect, the invention relates to a computer system for generating a fracability model of a subterranean formation. The computer system includes a processor and a memory coupled to the processor and storing instruction, the instructions, when executed by the processor, comprising functionality for coring and collecting rock cores from a plurality of geographical locations in the subterranean formation, capturing a plurality of core images of the rock cores, generating, based on the plurality of core images, a plurality of artificial fracture counts of the rock cores, computing, based on the plurality of artificial fracture counts, a first fracture density curve corresponding to a first geographical location of the plurality of geographical locations, generating, based on the first fracture density curve, a first fracability measure curve of the rock cores, and generating, based at least on the first fracability measure curve, a fracability model of the subterranean formation.

In general, in one aspect, the invention relates to a non-transitory computer readable medium storing instructions executable by a computer processor for generating a fracability model of a subterranean formation. The instructions includes functionality for coring and collecting rock cores from a plurality of geographical locations in the subterranean formation, capturing a plurality of core images of the rock cores, generating, based on the plurality of core images, a plurality of artificial fracture counts of the rock cores, computing, based on the plurality of artificial fracture counts, a first fracture density curve corresponding to a first geographical location of the plurality of geographical locations, generating, based on the first fracture density curve, a first fracability measure curve of the rock cores, and generating, based at least on the first fracability measure curve, a fracability model of the subterranean formation.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method, a system, and a non-transitory computer readable medium for measuring rock fracability based on artificial fracture density of rock cores of a subterranean formation. An artificial fracture is a fracture that is produced when coring bit applies stress to rocks downhole during coring to collect the rock core. Various number of artificial fractures may be present on the surface of the rock core that indicate the stress applied to the rock core during coring. Rock fracability is measured based on the presence of the artificial fractures. First, a series of cores from one specific well or multiple wells are collected with depth marked on the cores. Next, high resolution photographs of the collected cores are captured where artificial fractures are recognized and counted along the depth markings. Accordingly, the artificial fracture density is calculated to generate a fracture density curve based on the artificial fracture counts. The fracture density curve is then correlated to other mechanical properties and interpreted to quantify rock fracability. The measured rock fracability can be used to guide well drilling or develop a hydraulic fracturing plan. In one or more embodiments of the invention, the artificial fractures are automatically recognized and counted using artificial intelligence techniques.

Figure 1:
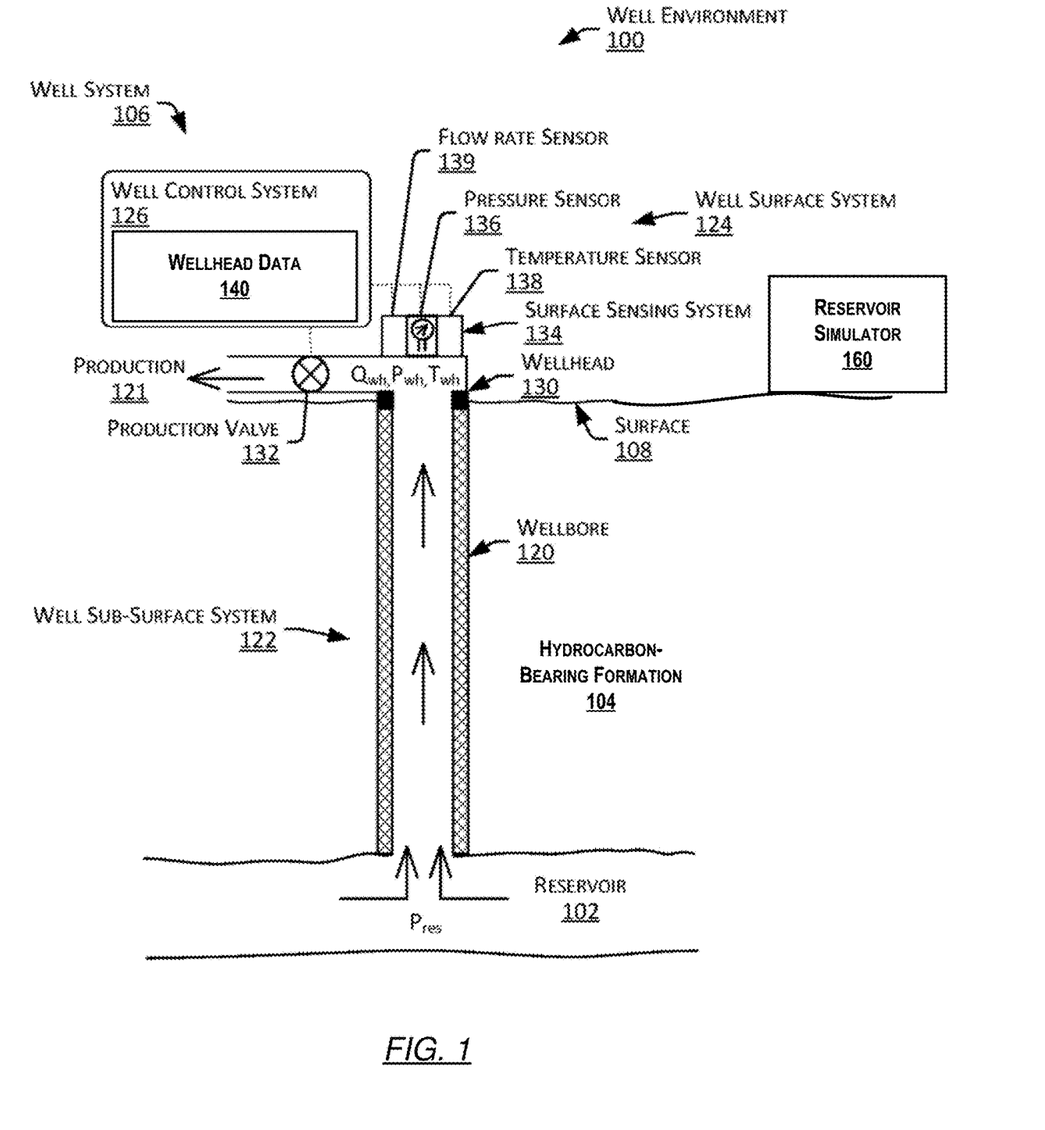
FIGS. 1 and 2 show systems in accordance with one or more embodiments.

Turning to FIG. 1, FIG. 1 shows a schematic diagram in accordance with one or more embodiments. As shown in FIG. 1, FIG. 1 illustrates a well environment (100) that includes a hydrocarbon reservoir ("reservoir") (102) located in a subsurface hydrocarbon-bearing formation ("formation") (104) and a well system (106). The hydrocarbon-bearing formation (104) may include a porous or fractured rock formation that resides underground, beneath the earth's surface ("surface") (108). In the case of the well system (106) being a hydrocarbon well, the reservoir (102) may include a portion of the hydrocarbon-bearing formation (104). The hydrocarbon-bearing formation (104) and the reservoir (102) may include different layers of rock having varying characteristics, such as varying degrees of permeability, porosity, capillary pressure, and resistivity. In the case of the well system (106) being operated as a production well, the well system (106) may facilitate the extraction of hydrocarbons (or "production") from the reservoir (102).

In some embodiments, the well system (106) includes a wellbore (120), a well sub-surface system (122), a well surface system (124), and a well control system ("control system") (126). The control system (126) may control various operations of the well system (106), such as well production operations, well completion operations, well maintenance operations, and reservoir monitoring, assessment and development operations. In some embodiments, the control system (126) includes a computer system that is the same as or similar to that of computer system (700) described below in FIGS. 7A and 7B and the accompanying description.

The wellbore (120) may include a bored hole that extends from the surface (108) into a target zone of the hydrocarbon-bearing formation (104), such as the reservoir (102). An upper end of the wellbore (120), terminating at or near the surface (108), may be referred to as the "up-hole" end of the wellbore (120), and a lower end of the wellbore, terminating in the hydrocarbon-bearing formation (104), may be referred to as the "down-hole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the hydrocarbon-bearing formation (104) or the reservoir (102) during injection operations, or the communication of monitoring devices (e.g., logging tools) into the hydrocarbon-bearing formation (104) or the reservoir (102) during monitoring operations (e.g., during in situ logging operations).

In some embodiments, during operation of the well system (106), the control system (126) collects and records wellhead data (140) for the well system (106). The wellhead data (140) may include, for example, a record of measurements of wellhead pressure ($P_{wh}$) (e.g., including flowing wellhead pressure), wellhead temperature ($T_{wh}$) (e.g., including flowing wellhead temperature), wellhead production rate ($Q_{wh}$) over some or all of the life of the well (106), and water cut data. In some embodiments, the measurements are recorded in real-time, and are available for review or use within seconds, minutes or hours of the condition being sensed (e.g., the measurements are available within 1 hour of the condition being sensed). In such an embodiment, the wellhead data (140) may be referred to as "real-time" wellhead data (140). Real-time wellhead data (140) may enable an operator of the well (106) to assess a relatively current state of the well system (106), and make real-time decisions regarding development of the well system (106) and the reservoir (102), such as on-demand adjustments in regulation of production flow from the well.

In some embodiments, the well sub-surface system (122) includes casing installed in the wellbore (120). For example, the wellbore (120) may have a cased portion and an uncased (or "open-hole") portion. The cased portion may include a portion of the wellbore having casing (e.g., casing pipe and casing cement) disposed therein. The uncased portion may include a portion of the wellbore not having casing disposed therein. In some embodiments, the casing includes an annular casing that lines the wall of the wellbore (120) to define a central passage that provides a conduit for the transport of tools and substances through the wellbore (120). For example, the central passage may provide a conduit for lowering logging tools into the wellbore (120), a conduit for the flow of production (121) (e.g., oil and gas) from the reservoir (102) to the surface (108), or a conduit for the flow of injection substances (e.g., water) from the surface (108) into the hydrocarbon-bearing formation (104). In some embodiments, the well sub-surface system (122) includes production tubing installed in the wellbore (120). The production tubing may provide a conduit for the transport of tools and substances through the wellbore (120). The production tubing may, for example, be disposed inside casing. In such an embodiment, the production tubing may provide a conduit for some or all of the production (121) (e.g., oil and gas) passing through the wellbore (120) and the casing.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more production valves (132) that are operable to control the flow of production (134). For example, a production valve (132) may be fully opened to enable unrestricted flow of production (121) from the wellbore (120), the production valve (132) may be partially opened to partially restrict (or "throttle") the flow of production (121) from the wellbore (120), and production valve (132) may be fully closed to fully restrict (or "block") the flow of production (121) from the wellbore (120), and through the well surface system (124).

In some embodiments, the wellhead (130) includes a choke assembly. For example, the choke assembly may include hardware with functionality for opening and closing the fluid flow through pipes in the well system (106). Likewise, the choke assembly may include a pipe manifold that may lower the pressure of fluid traversing the wellhead. As such, the choke assembly may include set of high pressure valves and at least two chokes. These chokes may be fixed or adjustable or a mix of both. Redundancy may be provided so that if one choke has to be taken out of service, the flow can be directed through another choke. In some embodiments, pressure valves and chokes are communicatively coupled to the well control system (126). Accordingly, a well control system (126) may obtain wellhead data regarding the choke assembly as well as transmit one or more commands to components within the choke assembly in order to adjust one or more choke assembly parameters.

Keeping with FIG. 1, in some embodiments, the well surface system (124) includes a surface sensing system (134). The surface sensing system (134) may include sensors for sensing characteristics of substances, including production (121), passing through or otherwise located in the well surface system (124). The characteristics may include, for example, pressure, temperature and flow rate of production (121) flowing through the wellhead (130), or other conduits of the well surface system (124), after exiting the wellbore (120).

In some embodiments, the surface sensing system (134) includes a surface pressure sensor (136) operable to sense the pressure of production (151) flowing through the well surface system (124), after it exits the wellbore (120). The surface pressure sensor (136) may include, for example, a wellhead pressure sensor that senses a pressure of production (121) flowing through or otherwise located in the wellhead (130). In some embodiments, the surface sensing system (134) includes a surface temperature sensor (138) operable to sense the temperature of production (151) flowing through the well surface system (124), after it exits the wellbore (120). The surface temperature sensor (138) may include, for example, a wellhead temperature sensor that senses a temperature of production (121) flowing through or otherwise located in the wellhead (130), referred to as "wellhead temperature" ($T_{wh}$). In some embodiments, the surface sensing system (134) includes a flow rate sensor (139) operable to sense the flow rate of production (151) flowing through the well surface system (124), after it exits the wellbore (120). The flow rate sensor (139) may include hardware that senses a flow rate of production (121) ($Q_{wh}$) passing through the wellhead (130).

In some embodiments, the well system (106) includes a reservoir simulator (160). For example, the reservoir simulator (160) may include hardware and/or software with functionality for generating one or more reservoir models regarding the hydrocarbon-bearing formation (104) and/or performing one or more reservoir simulations. For example, the reservoir simulator (160) may store well logs and data regarding core samples for performing simulations. A reservoir simulator may further analyze the well log data, the core sample data, seismic data, and/or other types of data to generate and/or update the one or more reservoir models. While the reservoir simulator (160) is shown at a well site, embodiments are contemplated where reservoir simulators are located away from well sites. In some embodiments, the reservoir simulator (160) may include a computer system that is similar to the computer system (800) described below with regard to FIGS. 7A and 7B and the accompanying description.

Keeping with reservoir simulators, a reservoir simulator may include functionality for solving well equations and reservoir equations separately, e.g., using Additive Schwartz methods. When the number of wells in a simulation is relatively small, computation time spent solving well equations may be a small fraction of the total computation time. However, in massive full-field simulations, where hundreds or thousands of wells are being simulated, the total computation time for solving well equations may increase considerably. This may be particularly true when a multi-segment well model is used as the number of unknown well parameters to be solved may be much larger than a conventional well model. As such, reservoir simulators may assign wells to computer processes in parallel computing tasks statically and/or dynamically. For example, at the beginning of a reservoir simulation, a well may be assigned to a single computer process that performs the computations necessary for this well. In some embodiments, placement of a well within a computer process may be independent of grid partitioning, e.g., whether the well is surrounded by fine-grid cells or coarsened grid blocks. During a simulation, a computer process may access both grid data for a reservoir model and well data. As such, well assignment may affect such parallel communication patterns and thereby may influence reservoir simulation performance.

In some embodiments, well assignment for parallel computer processes may include the case where a number of wells being simulated is greater than the number of computer processes involved in a reservoir simulation. Thus, multiple wells may be assigned to one computer process operating within a parallel processing stage. As wells may not need to be solved at all times during a reservoir simulation, e.g., only when the wells are producing or injecting, a situation may occur where one computer process is solving equations for multiple wells while a production well assigned to another computer process is inactive causing the computer process to be idle (i.e., waiting for the other computer processes to finish in the parallel processing stage).

Figure 2:
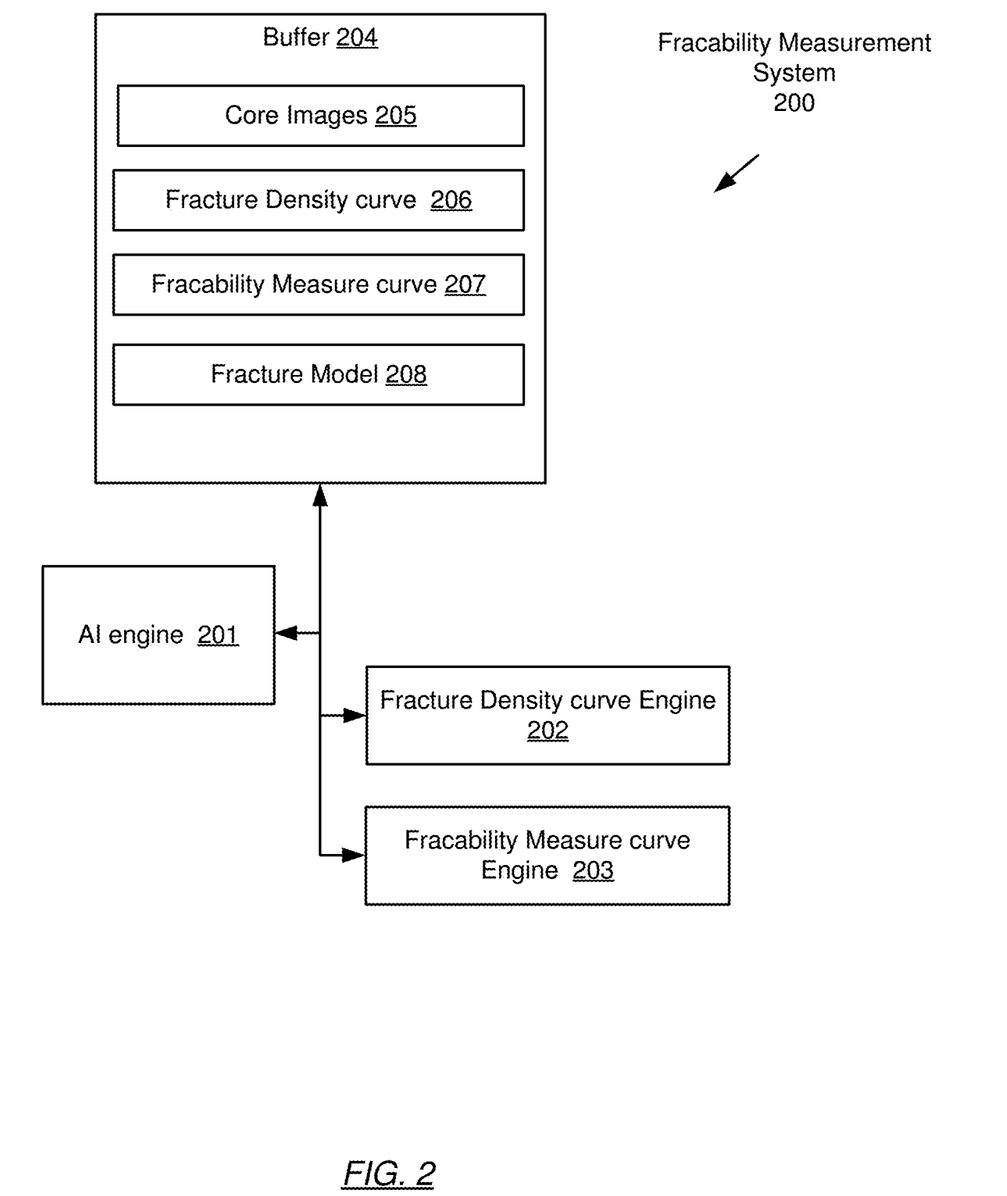

Turning to FIG. 2, FIG. 2 shows a schematic diagram in accordance with one or more embodiments. In one or more embodiments, one or more of the modules and/or elements shown in FIG. 2 may be omitted, repeated, and/or substituted. Accordingly, embodiments of the invention should not be considered limited to the specific arrangements of modules and/or elements shown in FIG. 2.

As shown in FIG. 2, FIG. 2 illustrates the fracability measurement system (200) that has multiple components, including, for example, a buffer (204), an artificial intelligence (AI) engine (201), a fracture density curve engine (202), and a fracability measure curve engine (203). Each of these components (201, 202, 203, 204) may be located on the same computing device (e.g., personal computer (PC), laptop, tablet PC, smart phone, multifunction printer, kiosk, server, etc.) or on different computing devices that are connected via a network, such as a wide area network or a portion of Internet of any size having wired and/or wireless segments. Each of these components is discussed below.

In one or more embodiments of the invention, the buffer (204) may be implemented in hardware (i.e., circuitry), software, or any combination thereof. The buffer (204) is configured to store data generated and/or used by the fracability measurement system (200). The data stored in the buffer (204) includes the core images (205), the fracture density curve (206), the fracability measure curve (207), and the fracture model (208).

The core images (205) are high resolution photographs of rock cores. The core images (205) include photographs of a number of rock core columns collected from different geographical locations throughout an area of interest. Each rock core column is a sequence of rock cores extending across a depth range of interest in the borehole. In particular, each rock core is marked to indicate the depths such that the depth markings are captured in the corresponding core image. In one or more embodiments of the invention, the core images (205) are captured using a three-dimensional (3D) scanner, a 3D camera, or other 3D photographing equipment. The width of each of core image (205) corresponds to the cylindrical circumference of the rock core column, or a portion of the circumference. The resolution of the core images (205) is selected such that structural details of the artificial fractures are sufficiently captured in the core images (205). Specifically, the structures of the artificial fractures are sufficiently clear in the core images (205) to be automatically recognized using machine learning techniques. In an example scenario, a core image corresponds to a portion of the length of a rock core. In another example, a core image may correspond to the length of two or more consecutive rock cores in the rock core column. Examples of the core images (205) are described in reference to FIG. 4 below.

The fracture density curve (206) is a curve of artificial fracture density as a function of depth. The artificial fracture density is a number of artificial fractures recognizable from the surface of the rock core and counted in a pre-determined depth window divided by the size (e.g., measured in ft) of the depth window. An example of the fracture density curve (206) is described in reference to FIG. 5 below.

The fracability measure curve (207) is a curve of fracability measure as a function of depth. The fracability measure is a measure of easiness to which the rock can be artificial fractured. For example, the fracability measure may be a ratio index with no unit. In another example, the fracability measure may be in the unit of $lb*in^{1/2}$. An example of correlating fracability measure is described in reference to FIG. 6 below.

The fracture model (208) is a machine learning model to recognize artificial fractures from the core images (205). In one or more embodiments of the invention, the fracture model (208) is trained, during a machine learning training phase, to include a signature of artificial fractures that is distinct from other structural features on the rock core surface that are not induced by the coring process. In one or more embodiments of the invention, the fracture model (208) is a neural network model.

In one or more embodiments of the invention, each of the AI engine (201), fracture density curve engine (202), and fracability measure curve engine (203) may be implemented in hardware (i.e., circuitry), software, or any combination thereof.

In one or more embodiments of the invention, the AI engine (201) is configured to generate the fracture model (208) based on a training set of core images (not shown). Each core image in the training set may have a similar format (e.g., resolution) as one of the core images (205). In contrast to the core images (205), each core image in the training set already includes confirmed artificial fractures and confirmed non-fracture features. A confirmed artificial fracture is a localized pattern in the core image that is confirmed by a user as representing an artificial fracture.

In one or more embodiments, the AI engine (201) is configured to recognize artificial fractures in the core images (205) based on the fracture model (208). In particular, the AI engine (201) identifies localized patterns in each of the core images (205) as artificial fractures that are distinct from a fracture barrier or other mechanical stratigraphy features. In one or more embodiments, the AI engine (201) recognizes artificial fractures in the core images (205) using a machine learning technique based on the aforementioned signature.

In one or more embodiments of the invention, the fracture density curve engine (202) is configured to generate the fracture density curve (206) based on the results of the AI engine (201). Specifically, the fracture density curve engine (202) counts the number of artificial fractures recognized by the AI engine (201). The recognized artificial fractures are counted over a moving depth window along the longitudinal direction of rock core column. In particular, the fracture density curve engine (202) identifies the depth markings in each of the core images (205) to interpolate and extrapolate a depth scale across consecutive core images. The number of artificial fractures within a pre-determined depth window (e.g., 1 ft, 5 ft, etc.) is counted and divided by the size of the depth window to generate an artificial fracture density. The depth window is moved to a next position such that consecutive artificial fracture densities are generated. As the depth window moves across the aforementioned depth range of interest, the fracture density curve is generated as the collection of individual artificial fracture densities with respect to corresponding depth window positions in the depth range of interest.

In one or more embodiments of the invention, the fracability measure curve engine (203) is configured to generate the fracability measure curve (207) based on the results of the fracture density curve engine (202). Specifically, the fracability measure curve engine (203) applies a mathematical smoothing function to the fracture density curve (206) to remove statistical anomalies. Further, the fracability measure curve engine (203) correlates the fracture density curve (206) and other mechanical properties (e.g., derived from well log measurements) of the subterranean formation where the rock cores are collected. The correlated results are used to determine the fracability measure as a function of depth over the depth range of interest.

In one or more embodiments, the fracability measurement system (200) performs the functionalities described above using the method described in reference to FIG. 3 below. Although the fracability measurement system (200) is shown as having three engines (201, 202, 203), in other embodiments of the invention, the fracability measurement system (200) may have more or fewer engines and/or more or fewer other components. Further, the functionality of each component described above may be split across components. Further still, each component (201, 202, 203) may be utilized multiple times to carry out an iterative operation.

Figure 3:
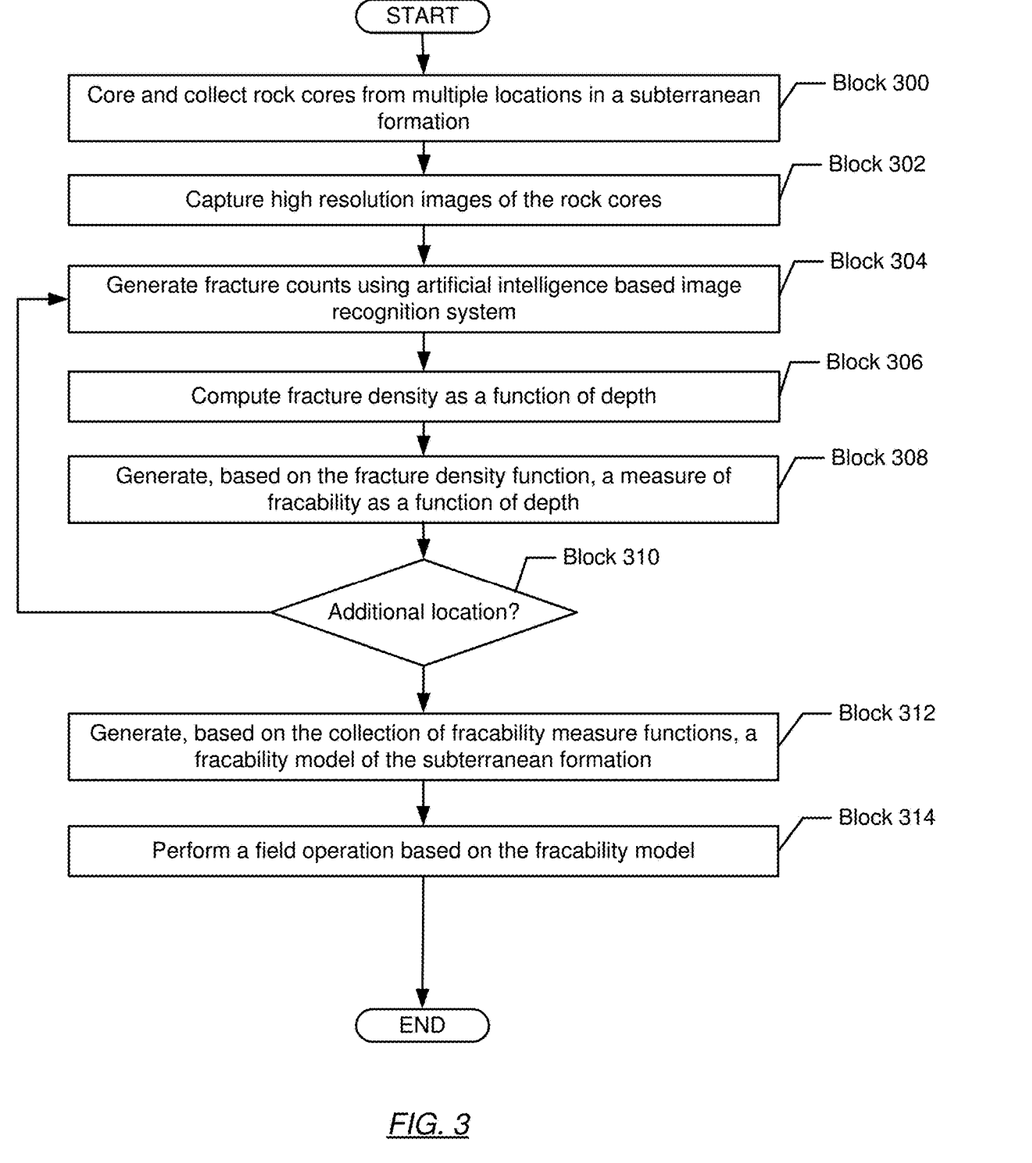
FIG. 3 shows a flowchart in accordance with one or more embodiments.

Turning to FIG. 3, FIG. 3 shows a flowchart in accordance with one or more embodiments. Specifically, FIG. 3 describes a method of generating a fracability model of a subterranean formation. One or more blocks in FIG. 3 may be performed using one or more components as described in FIGS. 1 and 2. While the various blocks in FIG. 3 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Initially in Block 300, coring is performed to collect rock cores from a number of geographical locations in the subterranean formation. The coring produces artificial fractures when coring bit applies stress to rocks downhole to collect the rock cores. The rock cores are laid out in a sequential order to form a contiguous column (referred to as a rock core column) according to respective depths where the rock cores are collected. One rock core column is laid out for each of the geographical locations where coring is performed.

In Block 302, high resolution photographs (i.e., core images) of consecutive sections of the rock core column are captured. The resolution of the photograph is selected such as to clearly delineate details of the artificial fractures. In one or more embodiments of the invention, a 3D scanner or camera is used to capture the high resolution photographs. For example, the 3D scanner may be rotated around the longitudinal axis of the rock core column. In another example, the 3D scanner may be stationery while the rock core column is rotated around the longitudinal axis. In either example, the optical sensor of the 3D scanner captures an image of a vertical section of the rock core column around the cylindrical circumference.

In Bock 304, the core images are analyzed to generate artificial fracture counts of the rock cores. In one or more embodiments, each artificial fracture count is the number of artificial fractures that are recognized and counted within a depth window. The depth window is moved along the longitudinal direction of the rock core column. An artificial intelligence (AI) fracture model is used to recognize and count the artificial fractures.

In Block 306, a fracture density curve is computed based on the artificial fracture counts. The artificial fracture count is recorded for each depth location where the moving depth window is positioned. Each recorded artificial fracture count is divided by the size of the depth window to compute the artificial fracture density. By moving the depth window across a depth range of interest, the successively recorded and computed artificial fracture densities form the fracture density curve as a function of depth. In this context, the fracture density curve is also referred to as the fracture density function. The fracture density curve is specific to the geographical location where coring is performed to create the rock core column.

In Block 308, a fracability measure curve of the rock cores is generated based on the fracture density curve. In one or more embodiments, the fracability measure curve is generated by applying a smoothing function to the fracture density curve and by correlating the fracture density curve to well log data collected from a corresponding borehole. For example, the smoothing function may be a moving average computed every five consecutive artificial fracture densities. The fracability measure curve is a function of depth and is also referred to as the fracability measure function In Block 310, a decision is made as to whether rock core images of additional geographical location(s) remain to be analyzed. If the decision is positive, i.e., rock core images of additional geographical location(s) remain to be analyzed, the method returns to Block 304 to process rock core images associated with a different geographical location. If the decision is negative, i.e., no more rock core images remain to be analyzed, the method proceeds to Block 312.

In Block 312, a fracability model of the subterranean formation is generated by combining the fracability measure curves of all geographical locations where coring was performed to collect the rock cores. In other words, the fracability model of the subterranean formation is the collection of the fracability measure curves of all geographical locations where coring was performed to collect the rock cores. In one or more embodiments, mathematical interpolation and/or extrapolation are applied to the collection of the fracability measure curves to expand the fracability model.

In Block 314, a field operation of the subterranean formation is performed based at least on the fracability model. In the fracability model, high fracability measure (i.e., high artificial fracture density) represents that rocks are easier to fracture and low fracability measure (i.e., low artificial fracture density) represents that rocks are difficult to fracture. The fracability measure is used to evaluate hydraulic fracturing quantitatively. Injectors for hydraulic fracturing may be placed in the interval (i.e., a section of the wellbore) with high artificial fracture density indicating high fracability. Further, injecting wells may be drilled in a geographical location where the fracability model indicates high fracability.

Figure 4:
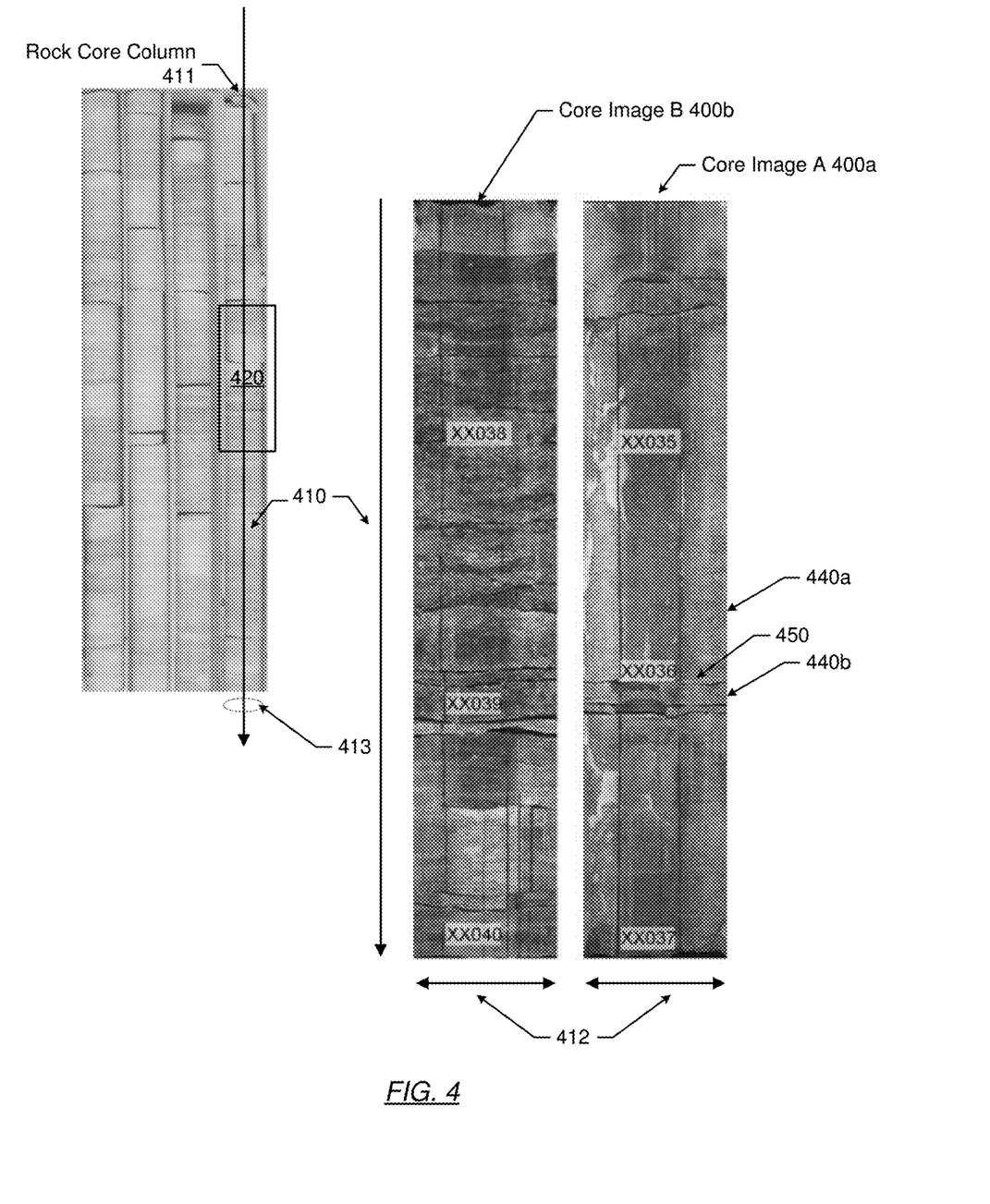
FIGS. 4, 5, and 6 show an example in accordance with one or more embodiments.
Figure 5:
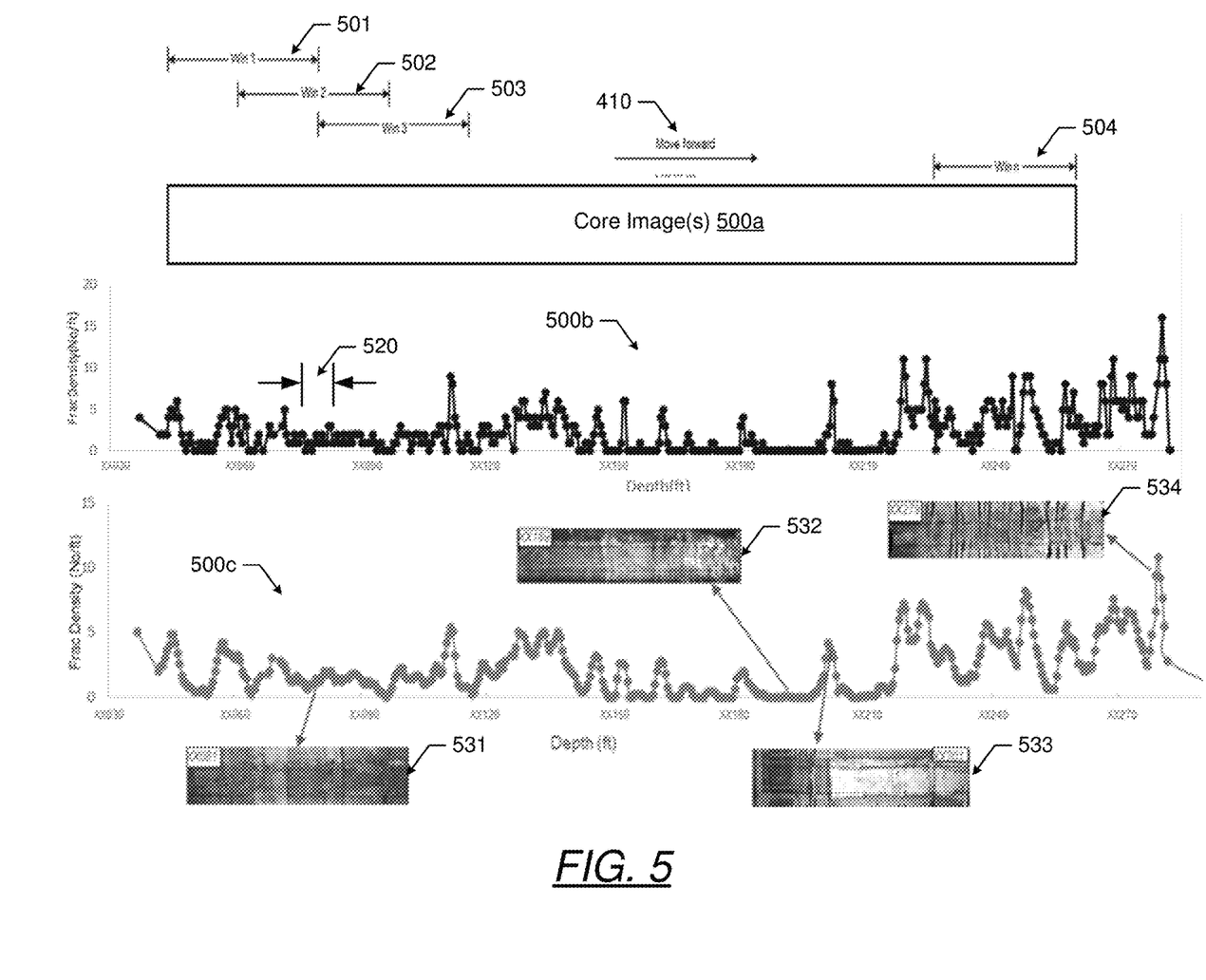
Figure 6:
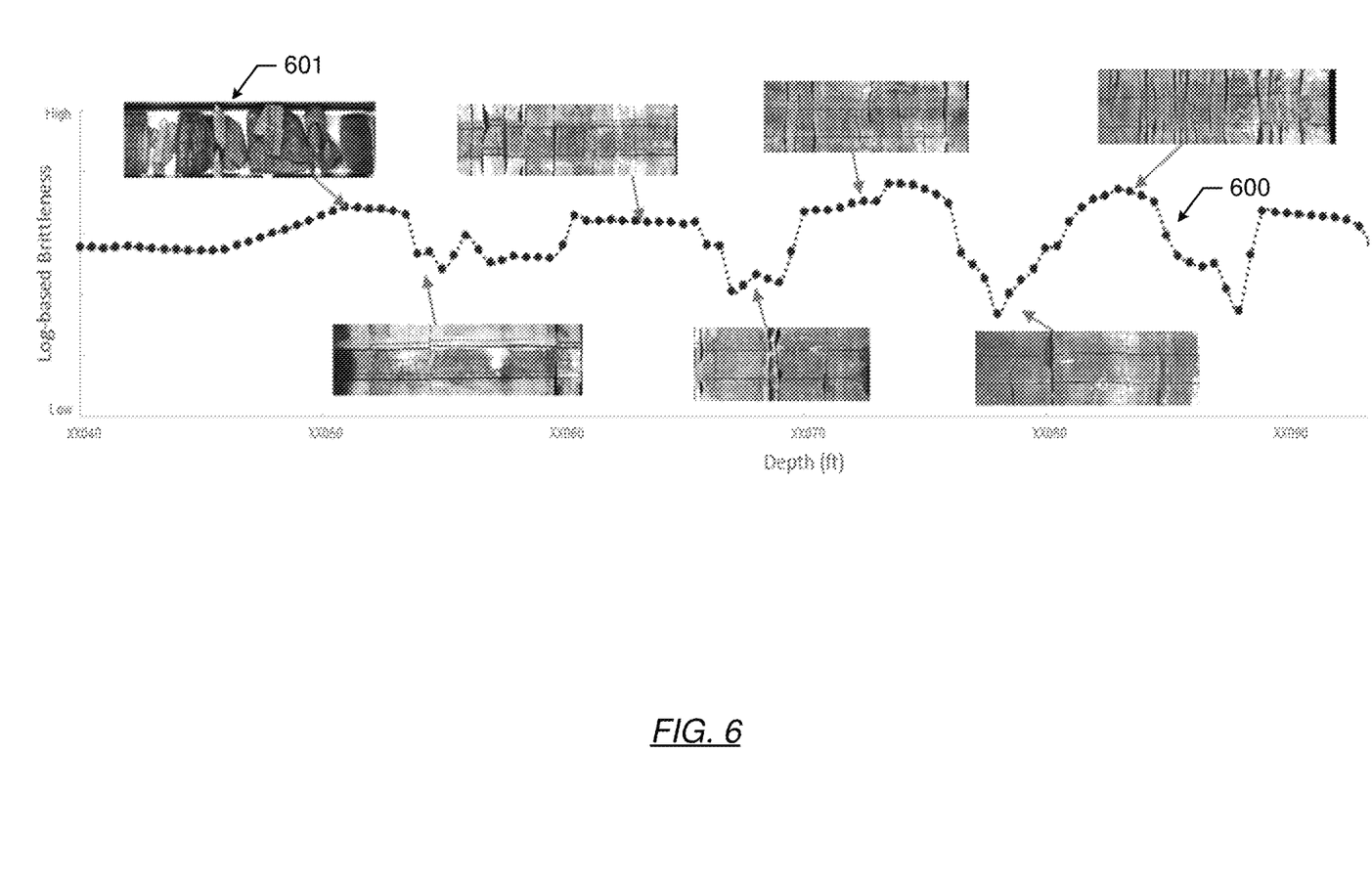

Turning to FIGS. 4-6, FIGS. 4-6 provides an example of generating a fracability model of a subterranean formation. The example shown in FIGS. 4-6 may be, for example, based on one or more components depicted in FIGS. 1-2 above and the method flowchart depicted in FIG. 3 above. In one or more embodiments, one or more of the modules and/or elements shown in FIGS. 4-6 may be omitted, repeated, and/or substituted. Accordingly, embodiments of the invention should not be considered limited to the specific arrangements of modules and/or elements shown in FIGS. 4-6.

As shown in FIG. 4, FIG. 4 illustrates a core image A (400a) and a core image B (400b) that are high resolution photographs of top and bottom halves of a section (420) of the rock core column (411). The width (412) of the core image A (400a) and core image B (400b) corresponds to the cylindrical circumference (413) of the rock core column (411). The four rock core columns shown in FIG. 4 are collected from boreholes at four different geographical locations in an area of interest of the subterranean formation. The arrow (410) represents the longitudinal direction along the borehole. The labels xx0035, xx0036, xx0037, xx0038, xx0039, and xx0040 are depth markers indicating the depth along the specific borehole where the rock core column (411) is collected. For example, the numerals in the depth markers may be in the units of feet. As described in reference to FIG. 3 above, artificial fractures are identified and counted in the core image A (400a) and core image B (400b) to generate a fracture density curve. For example, artificial fracture (450), among numerous other artificial fractures, are identified using an AI fracture model. Specifically, the artificial fracture (450) is a separation between the interval A (440a) and interval B (440b). The AI fracture model is used in object recognition to differentiate between artificial fractures and fracture barriers.

Turning to FIG. 5, FIG. 5 illustrates a schematic diagram of one or more core image(s) (500a), a fracture density curve (500b), and a smoothed fracture density curve (500c). The core image(s) (500a) may correspond to the core image A (400a), core image B (400b), or any other core images laid out in sequential order according to the depth markers. Artificial fractures are identified and counted based on the AI model within each of a sequence of moving depth windows (501, 502, 503, 504, etc.) along the longitudinal direction (410) of the core image (500a). The counted artificial fracture number is assigned to the center depth of the depth window. Adjacent depth windows are overlapped, e.g., by half the size of each depth window. The size of each depth window is specified (e.g., 1 foot, 2 feet, etc.) along the longitudinal direction (410). The artificial fracture count for each depth window is divided by the size of the corresponding depth window to compute the artificial fracture density. Accordingly, the computed artificial fracture densities (e.g., in unit of no. per foot or no./ft) are included in the fracture density curve (500b). The horizontal axis of the fracture density curve (500b) represents depth along the longitudinal direction (410). For example, the artificial fracture densities computed for all the depth windows within the core image A (400a) correspond to a portion (520) of the fracture density curve (500b). In other words, the fracture density curve (500b) is composed from a sequence of core images including the core image A (400a). Specifically, each dot on the fracture density curve (500b) corresponds to one depth window within one core image of the sequence. The smoothed fracture density curve (500c) is generated by applying a moving average algorithm to the fracture density curve (500b) to remove abnormal values. Each depth value along the horizontal axis of the smoothed fracture density curve (500c) corresponds to one particular depth window within one core image, such as core image (531), core image (532), core image (533), core image (534), etc. For example, the core image (531) may correspond to the core image A (400a) shown in FIG. 4 above.

Turning to FIG. 6, FIG. 6 illustrates a comparison between computed rock brittleness in a borehole and artificial fracture density of the rock core column. The horizontal axis represents the longitudinal direction along depth of the borehole while the vertical axis represents rock brittleness in a logarithmic scale. The rock brittleness values (600) are computed from well log data (e.g., density log, compressional wave and shear wave sonic log, etc.). As shown in FIG. 6, rock brittleness values (600) at various depths correlate well with artificial fracture densities generated from core images (e.g., core image (601)) based on the AI fracture model. In other words, the artificial fracture densities generated from core images (e.g., core image (601)) based on the AI fracture model may be used to compute a measure of rock brittleness as an alternative method to computing rock brittleness from well log data. In one or more embodiments, the computed measure of rock brittleness based on the AI fracture model is a measure of easiness to which the formation rock can be fractured. Accordingly, the computed measure of rock brittleness based on the AI fracture model is used as the fracability measure.

Figure 7A:
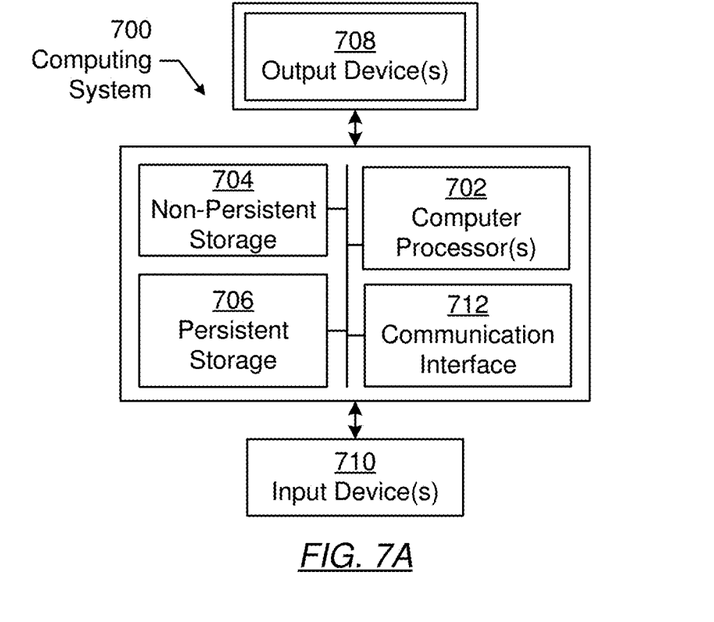
FIGS. 7A and 7B show a computing system in accordance with one or more embodiments.

Embodiments may be implemented on a computing system. Any combination of mobile, desktop, server, router, switch, embedded device, or other types of hardware may be used. For example, as shown in FIG. 7A, the computing system (700) may include one or more computer processors (702), non-persistent storage (704) (e.g., volatile memory, such as random access memory (RAM), cache memory), persistent storage (706) (e.g., a hard disk, an optical drive such as a compact disk (CD) drive or digital versatile disk (DVD) drive, a flash memory, etc.), a communication interface (712) (e.g., Bluetooth interface, infrared interface, network interface, optical interface, etc.), and numerous other elements and functionalities.

The computer processor(s) (702) may be an integrated circuit for processing instructions. For example, the computer processor(s) may be one or more cores or micro-cores of a processor. The computing system (700) may also include one or more input devices (710), such as a touchscreen, keyboard, mouse, microphone, touchpad, electronic pen, or any other type of input device.

The communication interface (712) may include an integrated circuit for connecting the computing system (700) to a network (not shown) (e.g., a local area network (LAN), a wide area network (WAN) such as the Internet, mobile network, or any other type of network) and/or to another device, such as another computing device.

Further, the computing system (700) may include one or more output devices (708), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (702), non-persistent storage (704), and persistent storage (706). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 7B:
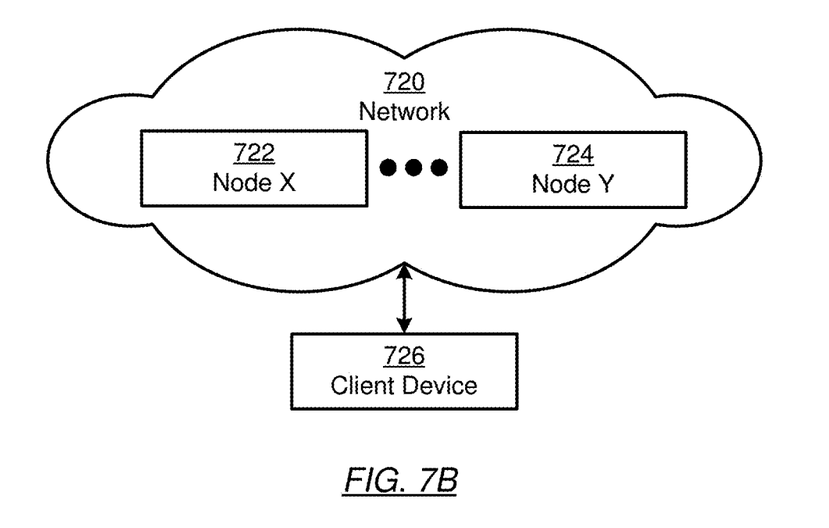

The computing system (700) in FIG. 7A may be connected to or be a part of a network. For example, as shown in FIG. 7B, the network (720) may include multiple nodes (e.g., node X (722), node Y (724)). Each node may correspond to a computing system, such as the computing system shown in FIG. 7A, or a group of nodes combined may correspond to the computing system shown in FIG. 7A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (700) may be located at a remote location and connected to the other elements over a network.

Although not shown in FIG. 7B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (722), node Y (724)) in the network (720) may be configured to provide services for a client device (726). For example, the nodes may be part of a cloud computing system. The nodes may include functionality to receive requests from the client device (726) and transmit responses to the client device (726). The client device (726) may be a computing system, such as the computing system shown in FIG. 7A. Further, the client device (726) may include and/or perform all or a portion of one or more embodiments of the disclosure.

The computing system or group of computing systems described in FIGS. 7A and 7B may include functionality to perform a variety of operations disclosed herein. For example, the computing system(s) may perform communication between processes on the same or different systems. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until the server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system (700) in FIG. 7A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail—such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 7A, while performing one or more embodiments of the disclosure, may perform data comparison. Data comparison may be used to compare two or more data values (e.g., A, B). For example, one or more embodiments may determine whether $A>B$, $A=B$, $A!=B$, $A<B$, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if $A>B$, B may be subtracted from A (i.e., A−B), and the status flags may be read to determine if the result is positive (i.e., if $A>B$, then $A-B>0$). In one or more embodiments, B may be considered a threshold, and A is deemed to satisfy the threshold if A=B or if A>B, as determined using the ALU. In one or more embodiments of the disclosure, A and B may be vectors, and comparing A with B includes comparing the first element of vector A with the first element of vector B, the second element of vector A with the second element of vector B, etc. In one or more embodiments, if A and B are strings, the binary values of the strings may be compared.

The computing system in FIG. 7A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 7A may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions presents only a few examples of functions performed by the computing system of FIG. 7A and the nodes and/or client device in FIG. 7B. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method for generating a fracability model of a subterranean formation, the method comprising:
   coring and collecting rock cores from a plurality of geographical locations in the subterranean formation, wherein each of the rock cores comprises artificial fractures produced when applying stress by a coring bit to downhole rocks to collect the rock cores;
   capturing a plurality of core images of the rock cores that are brought to the Earth's surface;
   generating, by a computer processor and based on the plurality of core images, a plurality of artificial fracture counts of the rock cores, wherein the plurality of artificial fracture counts are generated by counting the artificial fractures in the plurality of core images captured from the rock cores at the Earth's surface using an artificial intelligence (AI) fracture model that recognizes and counts the artificial fractures;
   computing, by the computer processor and based on the plurality of artificial fracture counts, a first fracture density curve corresponding to a first geographical location of the plurality of geographical locations;
   generating, by the computer processor and based on the first fracture density curve, a first fracability measure curve of the rock cores; and
   generating, by the computer processor and based at least on the first fracability measure curve, a fracability model of the subterranean formation.

2. The method according to claim 1, further comprising:
computing, by the computer processor and based on the plurality of artificial fracture counts, a second fracture density curve corresponding to a second geographical location of the plurality of geographical locations; and
generating, by the computer processor and based on the second fracture density curve, a second fracability measure curve of the rock cores,
wherein generating the fracability model is further based on the second fracability measure curve.

3. The method according to claim 1, further comprising:
generating, based on the plurality of core images, the AI fracture model of the rock cores.

4. The method according to claim 3,
wherein the AI fracture model is trained, during a machine learning training phase, based on distinct characteristics of the artificial fractures and a fracture barrier.

5. The method according to claim 1, wherein computing the first fracture density curve comprises:
generating a first artificial fracture count corresponding to a pre-determined depth window at a first depth along one or more rock cores of the first geographical location; and
generating a second artificial fracture count corresponding to the pre-determined depth window at a second depth along the one or more rock cores of the first geographical location,
wherein the first depth and the second depth are separated by half of the pre-determined depth window.

6. The method according to claim 5, wherein generating the first fracability measure curve comprising:
applying a mathematical smoothing function to the first fracture density curve.

7. The method according to claim 1, further comprising:
performing, based at least on the fracability model, a field operation of the subterranean formation.

8. A computer system for generating a fracability model of a subterranean formation, comprising:
a processor; and
a memory coupled to the processor and storing instruction, the instructions, when executed by the processor, comprising functionality for:
coring and collecting rock cores from a plurality of geographical locations in the subterranean formation, wherein each of the rock cores comprises artificial fractures produced when applying stress by a coring bit to downhole rocks to collect the rock cores;
capturing a plurality of core images of the rock cores that are brought to the Earth's surface;
generating, based on the plurality of core images, a plurality of artificial fracture counts of the rock cores, wherein the plurality of artificial fracture counts are generated by counting the artificial fractures in the plurality of core images captured from the rock cores at the Earth's surface using an artificial intelligence (AI) fracture model that recognizes and counts the artificial fractures;
computing, based on the plurality of artificial fracture counts, a first fracture density curve corresponding to a first geographical location of the plurality of geographical locations;
generating, based on the first fracture density curve, a first fracability measure curve of the rock cores; and
generating, based at least on the first fracability measure curve, a fracability model of the subterranean formation.

9. The computer system according to claim 8, the instructions, when executed by the processor, further comprising functionality for:
computing, based on the plurality of artificial fracture counts, a second fracture density curve corresponding to a second geographical location of the plurality of geographical locations; and
generating, based on the second fracture density curve, a second fracability measure curve of the rock cores,
wherein generating the fracability model is further based on the second fracability measure curve.

10. The computer system according to claim 8, the instructions, when executed by the processor, further comprising functionality for:
generating, based on the plurality of core images, the AI fracture model of the rock cores.

11. The computer system according to claim 10,
wherein the AI fracture model is trained, during a machine learning training phase, based on distinct characteristics of the artificial fracture and a fracture barrier.

12. The computer system according to claim 8, wherein computing the first fracture density curve comprises:
generating a first artificial fracture count corresponding to a pre-determined depth window at a first depth along one or more rock cores of the first geographical location; and
generating a second artificial fracture count corresponding to the pre-determined depth window at a second depth along the one or more rock cores of the first geographical location,
wherein the first depth and the second depth are separated by half of the pre-determined depth window.

13. The computer system according to claim 12, wherein generating the first fracability measure curve comprising:
applying a mathematical smoothing function to the first fracture density curve.

14. The computer system according to claim 8, the instructions, when executed by the processor, further comprising functionality for:
performing, based at least on the fracability model, a field operation of the subterranean formation.

15. A non-transitory computer readable medium storing instructions executable by a computer processor for generating a fracability model of a subterranean formation, the instructions comprising functionality for:
coring subterranean formation, wherein each of the rock cores comprises artificial fractures produced when applying stress by a coring bit to downhole rocks to collect the rock cores;
capturing a plurality of core images of the rock cores that are brought to the Earth's surface;
generating, based on the plurality of core images, a plurality of artificial fracture counts of the rock cores, wherein the plurality of artificial fracture counts are generated by counting the artificial fractures in the plurality of core images captured from the rock cores at the Earth's surface using an artificial intelligence (AI) fracture model that recognizes and counts the artificial fractures;
computing, based on the plurality of artificial fracture counts, a first fracture density curve corresponding to a first geographical location of the plurality of geographical locations;
generating, based on the first fracture density curve, a first fracability measure curve of the rock cores; and generating, based at least on the first fracability measure curve, a fracability model of the subterranean formation.

16. The non-transitory computer readable medium according to claim 15, the instructions further comprising functionality for:
   computing, based on the plurality of artificial fracture counts, a second fracture density curve corresponding to a second geographical location of the plurality of geographical locations; and
   generating, based on the second fracture density curve, a second fracability measure curve of the rock cores,
   wherein generating the fracability model is further based on the second fracability measure curve.

17. The non-transitory computer readable medium according to claim 15, the instructions further comprising functionality for:
   generating, based on the plurality of core images, the AI fracture model of the rock cores.

18. The non-transitory computer readable medium according to claim 17, wherein the AI fracture model is trained, during a machine learning training phase, based on distinct characteristics of the artificial fracture and a fracture barrier.

19. The non-transitory computer readable medium according to claim 15, wherein computing the first fracture density curve comprises:
   generating a first artificial fracture count corresponding to a pre-determined depth window at a first depth along one or more rock cores of the first geographical location; and
   generating a second artificial fracture count corresponding to the pre-determined depth window at a second depth along the one or more rock cores of the first geographical location,
   wherein the first depth and the second depth are separated by half of the pre-determined depth window.

20. The non-transitory computer readable medium according to claim 19, wherein generating the first fracability measure curve comprising:
   applying a mathematical smoothing function to the first fracture density curve.

* * * * *